United States Patent
Yonezawa et al.

(10) Patent No.: US 7,906,618 B2
(45) Date of Patent: Mar. 15, 2011

(54) PEPTIDE CAPABLE OF BINDING TO INSULIN-BINDING PROTEIN AND ADSORBENT

(75) Inventors: Ai Yonezawa, Osaka (JP); Souichi Morikawa, Hyogo (JP); Eiji Ogino, Osaka (JP)

(73) Assignee: Kaneka Corporation, Kita-ku, Osaka-shi (JP)

( * ) Notice: Subject to any disclaimer, the term of this patent is extended or adjusted under 35 U.S.C. 154(b) by 821 days.

(21) Appl. No.: 11/573,834

(22) PCT Filed: Aug. 9, 2005

(86) PCT No.: PCT/JP2005/014596
§ 371 (c)(1),
(2), (4) Date: Sep. 14, 2007

(87) PCT Pub. No.: WO2006/019015
PCT Pub. Date: Feb. 23, 2006

(65) Prior Publication Data
US 2008/0132679 A1 Jun. 5, 2008

(30) Foreign Application Priority Data
Aug. 18, 2004 (JP) .................... 2004-237940

(51) Int. Cl.
*A61K 38/00* (2006.01)
*A61K 51/00* (2006.01)
(52) U.S. Cl. .............. 530/326; 514/1.1; 424/1.69

(58) Field of Classification Search .............. None
See application file for complete search history.

(56) References Cited

U.S. PATENT DOCUMENTS
5,422,339 A    6/1995   Eisenbarth et al.

FOREIGN PATENT DOCUMENTS
WO   WO-90/12814        11/1990
WO   WO-00/33068         6/2000
WO   WO-02/094344 A2    11/2002

OTHER PUBLICATIONS

International Preliminary Report on Patentability for PCT/JP2005/014596, dated Mar. 3, 2006, 7 pages.
Supplementary Partial European Search Report for counterpart EP Application No. 05770543.6, issued Sep. 20, 2007, 8 pages.
XP 002450105, Colon et al., Comparative peptidomics of the endocrine pancreas: islet hormones from the clawed frog *Xenopus laevis* and the red-bellied newt *Cynops pyrrhogaster*, Journal of Endocrinology, (2002), 175, pp. 769-777.

*Primary Examiner* — Maury Audet
(74) *Attorney, Agent, or Firm* — Connolly Bove Lodge & Hutz LLP

(57) ABSTRACT

The present invention relates to a peptide excellently capable of binding to a protein capable of binding to insulin (IBP), an adsorbent comprising the aforementioned peptide immobilized on a carrier, an adsorber comprising the aforementioned adsorbent, and a method of adsorbing IBPs by using the aforementioned adsorbent or adsorber.
The peptide, adsorbent, adsorber and method provided by the present invention can selectively adsorb and remove IBPs efficiently, and therefore be used, for example, in the treatment of diseases, typically diabetes, in which such IBP acts as an aggravating factor.

4 Claims, 2 Drawing Sheets

PEPTIDE CAPABLE OF BINDING TO INSULIN-BINDING PROTEIN AND ADSORBENT

CROSS-REFERENCE TO RELATED APPLICATIONS

This application is a National Stage of PCT/JP2005/014596 filed Aug. 9, 2005 which in turn claims priority from Japanese Application 2004-237940, filed Aug. 18, 2004 disclosures of which are incorporated herein by reference.

TECHNICAL FIELD

The present invention relates to a peptide capable of binding to a protein capable of binding to insulin (insulin-binding protein: hereinafter referred to as "IBP") occurring in body fluids (e.g. blood, plasma, etc.), an adsorbent comprising the aforementioned peptide immobilized on a carrier, an adsorber comprising the aforementioned adsorbent, and a method of adsorbing IBPs by using the aforementioned adsorbent or adsorber.

The peptide, adsorbent, adsorber and method provided by the present invention can be used, for example, in the treatment of diseases, typically diabetes, in which such IBP acts as an aggravating factor.

BACKGROUND ART

In spite of the recent remarkable progress of medical technology, various adult diseases, such as malignant tumors, arteriosclerosis and articular rheumatism, have become serious social problems. Diabetes, among others, is a disease causing a number of severe angiopathies such as cerebrovascular disorders and ischemic heart diseases and the number of patients with latent diabetes is especially large.

According to a broad classification made by the World Health Organization (WHO), diabetes includes type I diabetes mellitus (insulin-dependent diabetes; IDDM) caused by an absolute deficiency in insulin and type II diabetes mellitus (non-insulin-dependent diabetes; NIDDM) resulting from a relative deficiency in insulin. As main chronic complications, there may be mentioned neuropathy, retinopathy and nephropathy, among others, and, in all of these diseases, hyperglycemia is the principal causative factor. In particular, diabetic nephropathy, at an advanced stage, results in renal failure, for which dialysis therapy is necessary, and the five year survival rate after the start of dialysis is about 50%, which is very low as compared with that in non-diabetics, and patients with diabetic nephropathy still have a poor prognosis. Meanwhile, in 1998, the yearly number of patients newly submitted to dialysis therapy ranked above that of patients with chronic glomerulonephritis and, thus, diabetic nephropathy occupied the first place among causative diseases; that number has been increasing year after year (Non-Patent Document 1).

Type II diabetes is considered to be induced by a relative decrease in insulin secretion, together with an increase in insulin resistance as resulting from obesity, overeating, lack of exercise, stress and like other environmental factors. It is known that this insulin resistance is widely involved not only in diabetes but also in the onset and progress of some other disease such as arteriosclerosis and, as for the main cause thereof, it is known that a certain abnormality is seen in each stage of glucose metabolism.

The insulin receptor selectively binding to insulin and playing a role in the uptake of glucose into the cell in glucose metabolism is a tetramer glycoprotein composed of two α subunits having a molecular weight of about 135,000 and two β-subunits having a molecular weight of about 95,000 as coupled together by S—S bonding and occurring in the cell membrane of most cells in the body. Since the 1970's, a large number of studies have been made about the structure and other features thereof (Non-Patent Document 2).

On the other hand, it has been reported that a physiologically active substance like the insulin receptor on the cell occurs in body fluids. That substance is considered to be the complete or partly deficient insulin receptor or the like (soluble insulin receptor) excessively expressed in body fluids from some or other cause and it is known that this causes hyperinsulinemia or causes increased glucose production in the liver to bring about a hyperglycemic condition (Non-Patent Document 3). Patent Document 1 discloses a method of removing insulin-binding proteins but does not disclose any specific peptide.

When such a soluble insulin receptor as mentioned above is present in body fluids, it binds to insulin in the body fluid and thus inhibits the insulin activity, possibly causing insulin resistance.

There is no effective method of treatment found as yet against IBPs, including this soluble insulin receptor and the like, although there are several types of insulin resistance lowering agents.

Also there are several peptides having insulin activity and used as drugs but any peptide incapable of binding to other proteins (albumin etc.) in contact with body fluids, namely improved in selectivity, has not been found out as yet.

Patent Document 1: WO 02/094344

Non-Patent Document 1: Toseki Kaishi (Journal of the Japanese Society for Dialysis Therapy) 37 (1) (2004) 1-24

Non-Patent Document 2: J. Biol. Chem. 278 (2003) 27329-27332

Non-Patent Document 3: Diabetes 43 (1994) 143-153

SUMMARY OF THE INVENTION

In view of such problems, the present invention provides a peptide capable of binding to IBPs occurring in body fluids (e.g. blood, plasma, etc.) and an IBP adsorbent capable of selectively adsorbing IBPs efficiently using that peptide and, further provides an adsorber in which this adsorbent is used, and a method of adsorbing IBPs.

The present inventors made intensive investigations to accomplish the above object and found out peptides capable of binding to IBPs and incapable of adsorbing such proteins as albumin. Based on such finding, they have now completed the present invention.

Thus, the invention consists in a peptide which comprises the amino acid sequence of the following formula (I):

$$X01-[X02-L-X03-X04-X05-X06-N-[X07]_m]_n-X08 \quad (I)$$

(in the formula (I),

X01=C, K, or missing; wherein the amino group may be substituted by an acetyl or biotinyl group;

X02=Q, D, E, G, N, or missing;

X03=E, or D;

X04=N, D, E, G, Q, or missing;

X05=Y, F, S, T, W, or missing;

X06=C, A, G, M, S, or missing;

X07=a spacer, a linker, or missing;

X08=C, K, or missing; wherein the carboxyl group may be substituted by an amido group or a free acid;

m represents an integer not smaller than 0;

n represents an integer not smaller than 1; and
the case of the amino acid sequence becoming QLENYCN is
    excluded).
The present invention also consists in
a peptide
which comprises the amino acid sequence of the following
formula (II):

$$\text{U01-[E-Q-U02-U03-U04-U05-[U06]}_m]_n\text{-U07} \quad (II)$$

(in the formula (II),
U01=C, K, or missing; wherein the amino group may be
    substituted by an acetyl or biotinyl group;
U02=C, A, G, M, S, or missing;
U03=C, A, G, M, S, or missing;
U04=T, F, H, S, W, Y, or missing;
U05=S, D, E, N, Q, T, or missing;
U06=a spacer, a linker, or missing;
U07=C, K, or missing; wherein the carboxyl group may be
    substituted by an amido group or a free acid;
m represents an integer not smaller than 0;
n represents an integer not smaller than 1; and
the case of the amino acid sequence becoming EQCCTSIC is
    excluded).
The present invention further consists in
a peptide
which comprises the amino acid sequence of the following
formula (III):

$$\text{Z01-Z02-S-Z03-Z04-V-E-Z05-Z06-Y-Z07-Z08-Z09-Z10-Z11-Z12} \quad (III)$$

(in the formula (III),
Z01=C, K, or missing; wherein the amino group may be
    substituted by an acetyl or biotinyl group;
Z02=G, A, or missing;
Z03=H, D, or E;
Z04=L, I, or V;
Z05=A, G, I, L, or V;
Z06=L, A, I, or V;
Z07=L, I, or V;
Z08=V, A, G, I, L, or missing;
Z09=C, A, G, L, or missing;
Z10=G, A, or missing;
Z11=E, D, or missing;
Z12=R, K, or missing; and
the case of the amino acid sequence becoming
    CGSHLVEALYLVCGER is excluded).
Further, the invention consists in
an adsorbent for insulin-binding proteins
which comprises any of the above-mentioned peptides
immobilized on a water-insoluble carrier.
Further, the invention consists in
an adsorber for insulin-binding proteins
which comprises the above-mentioned adsorbent contained in a container having a liquid inlet and a liquid outlet
and equipped with means for preventing the adsorbent from
flowing out of the container.
Furthermore, the invention consists in
a method of adsorbing insulin-binding proteins
which comprises the step of contacting an insulin-binding
protein-containing liquid with the above-mentioned adsorbent.

EFFECT OF THE INVENTION

As is evident from the modes of embodiment and the
examples, which are to be described hereinbelow, a peptide
selectively binding to IBPs occurring in body fluids, and a
novel adsorbent in which the peptide is used and which can
adsorb IBPs are provided in accordance with the invention.
Further, by using devices for body fluid treatment which are
packed with the above-mentioned adsorbents, it is possible to
selectively removing IBPs from treatment target fluids such
as blood, plasma and serum.
In the following, the present invention is described in
detail. The description which follows is, however, by no
means limitative of the scope of the invention.

DETAILED DESCRIPTION OF THE INVENTION

In the present specification, the following abbreviations are
used to describe various amino acid residues. A: L-alanine
residue, C: L-cysteine residue, D: L-aspartic acid residue, E:
L-glutamic acid residue, F: L-phenylalanine residue, G:
L-glycine residue, H: L-histidine residue, I: L-isoleucine residue, K: L-lysine residue, L: L-leucine residue, M: L-methionine residue, N: L-aspartic acid residue, P: L-proline residue,
Q: L-glutamine residue, R: L-arginine residue, S: L-serine
residue, T: L-threonine residue, V: L-valine residue, W:
L-tryptophan residue, Y: L-tyrosine residue. In the present
specification, the amino acid sequence of each peptide is
described in the conventional manner, with the amino terminus (N terminus) located on the left side and the carboxyl
terminus (C terminus) on the right side.
The IBPs to be removed in the practice of the invention
include, but are not limited to, the following several groups:
(1) Complete or partly deficient soluble insulin receptor,
(2) Anti-insulin antibodies (which may belong to the class
    IgG, IgM, IgD, IgA, or IgE),
(3) Complete or partly deficient soluble insulin-like growth
    factor I receptor, or II receptor,
(4) Anti-insulin-like growth factor I, or II antibodies (which
    may belong to the class IgG, IgM, IgD, IgA, or IgE),
(5) Insulin-like growth factor-binding protein 1, 2, 3, 4, 5, or
    6,
(7) Insulin-like growth factor-binding protein-related proteins (IGFBPrp) such as insulin-like growth factor-binding
    proteins 7, 8, 9, and 10, and
(8) Proteins comprising at least one of those enumerated
    above, or complexes comprising at least one of them,
    among others.
Thus, all insulin resistance-inducing substances capable of
binding to insulin occurring mainly in body fluids to thereby
substantially inhibit the desired activity intrinsic in insulin are
included among the IBPs.
The peptides of the invention are capable of binding to
IBPs. The dissociation constant (KD) between each of them
and each IBP is preferably not higher than 1.0E–04, more
preferably not higher than 1.0E–05, still more preferably not
higher than 1.0E–06.
It is also preferred that the peptides each specifically bind
to a specific IBP. The "peptides" so referred to herein include
not only peptides derived from amino acids alone by peptide
bonds but also the so-called modified peptides, namely peptides optionally substituted and/or optionally coupled with a
non-peptide compound.
As the peptides of the invention, there may be mentioned,
for example, peptides comprising the amino acid sequence
represented by the following formula (I):

$$\text{X01-[X02-L-X03-X04-X05-X06-N-[X07]}_m]_n\text{-X08} \quad (I)$$

In the formula (I),
X01=C, K, or missing; wherein the amino group may be
    substituted by an acetyl or biotinyl group;
X02=Q, D, E, G, N, or missing;

X03=E, or D;
X04=N, D, E, G, Q, or missing;
X05=Y, F, S, T, W, or missing;
X06=C, A, G, M, S, or missing;
X07=a spacer, a linker, or missing;
X08=C, K, or missing; wherein the carboxyl group may be substituted by an amido group or a free acid;
m represents an integer not smaller than 0; and
n represents an integer not smaller than 1. The case of the amino acid sequence becoming QLENYCN (SEQ ID NO:1) is excluded.

Preferred as the peptides represented by the above formula (1) are peptides comprising the amino acid sequence CQLDNYAN (SEQ ID NO:2), CNLEQYAN (SEQ ID NO:3), CGLEGTMN (SEQ ID NO:4), CGLDNGLDN (SEQ ID NO:5) or LENALEN (SEQ ID NO:6).

More preferred are peptides consisting of the amino acid sequence CQLDNYAN (SEQ ID NO:2), CNLEQYAN (SEQ ID NO:3), CGLEGTMN (SEQ ID NO:4), CGLDNGLDN (SEQ ID NO:5) or LENALEN (SEQ ID NO:6).

As other examples of the peptides of the invention, there may be mentioned peptides comprising the amino acid sequence represented by the following formula (II):

U01-[E-Q-U02-U03-U04-U05-[U06]$_m$]$_n$-U07    (II)

In the formula (II),
U01=C, K, or missing; wherein the amino group may be substituted by an acetyl or biotinyl group;
U02=C, A, G, M, S, or missing;
U03=C, A, G, M, S, or missing;
U04=T, F, H, S, W, Y, or missing;
U05=S, D, E, N, Q, T, or missing;
U06=a spacer, a linker, or missing;
U07=C, K, or missing; wherein the carboxyl group may be substituted by an amido group or a free acid;
m represents an integer not smaller than 0; and
n represents an integer not smaller than 1. The case of the amino acid sequence becoming EQCCTSIC (SEQ ID NO:7) is excluded.

Preferred as the peptides comprising the amino acid sequence represented by the above formula (II) are peptides comprising the amino acid sequence CEQAATS (SEQ ID NO:8), CEQAGTS (SEQ ID NO:9), CEQMMHN (SEQ ID NO:10) or EQCCHN (SEQ ID NO:11). More preferred are peptides consisting of the amino acid sequence CEQAATS (SEQ ID NO:8), CEQAGTS (SEQ ID NO:9), CEQMMHN (SEQ ID NO:10) or EQCCHN (SEQ ID NO:11).

As further examples of the peptides of the invention, there may be mentioned peptides comprising the amino acid sequence represented by the following formula (III):

Z01-Z02-S-Z03-Z04-V-E-Z05-Z06-Y-Z07-Z08-Z09-Z10-Z11-Z12    (III)

In the formula (III),
Z01=C, K, or missing; wherein the amino group may be substituted by an acetyl or biotinyl group;
Z02=G, A, or missing;
Z03=H, D or E;
Z04=L, I or V;
Z05=A, G, I, L, or V;
Z06=L, A, I, or V;
Z07=L, I, or V;
Z08=V, A, G, I, L, or missing;
Z09=C, A, G, L, or missing;
Z10=G, A, or missing;
Z11=E, D, or missing; and
Z12=R, K, or missing. The case of the amino acid sequence becoming CGSHLVEALYLVCGER (SEQ ID NO:12) is excluded.

Preferred are peptides comprising the amino acid sequence of the above formula (III) in which Z01=C, K, or missing; wherein the amino group may be substituted by an acetyl or biotinyl group;
Z02=G, A, or missing (when Z01=C, however, Z02=A, or missing);
Z03=H, D, or E (when Z02=G, however, Z03=D, or E);
Z04=I or V;
Z05=G, I, L, or V;
Z06=L, A, I, or V;
Z07=L, I, or V (when Z06=L, however, Z07=I, or V);
Z08=V, A, G, I, L, or missing (when Z07=L, however, Z08=A, G, I, L, or missing);
Z09=C, A, G, L, or missing;
Z10=G, A, or missing (when Z08=V and Z9=C, however, Z10=A, or missing);
Z11=E, D, or missing (when Z9=C and Z10=G, however, Z11=D, or missing); and
Z12=R, K, or missing (when Z10=G and Z11=E, however, Z12=K, or missing).

More preferred are peptides comprising the amino acid sequence CASDIVEGLYIVLAER (SEQ ID NO:14), CASDIVEGIYL (SEQ ID NO:15), CASHIVEGIYLILAER (SEQ ID NO:16), CASHIVEGLYIVCAER (SEQ ID NO:17), CASHIVEGIYLACGDR (SEQ ID NO:18), GSDIVEGLYIVCAER (SEQ ID NO:19), GSDIVEGIYLALGEK (SEQ ID NO:20), or CQHILGSDIVEGIYL (SEQ ID NO:21).

Further more preferred are peptides consisting of the amino acid sequence CASDIVEGLYIVLAER(SEQ ID NO:14), CASDIVEGIYL (SEQ ID NO:15), CASHIVEGIYLILAER (SEQ ID NO:16), CASHIVEGLYIVCAER (SEQ ID NO:17), CASHIVEGIYLACGDR (SEQ ID NO:18), GSDIVEGLYIVCAER(SEQ ID NO:19), GSDIVEGIYLALGEK (SEQ ID NO:20), or CQHILGSDIVEGIYL (SEQ ID NO:21).

In the practice of the invention, the above-mentioned peptides or partial peptides thereof can be used each as a single species for IBP adsorption. It is also possible to use a mixture of two or more of the above-mentioned peptides or partial peptides thereof for IBP adsorption.

In the practice of the invention, it is further possible to link two or more of the above-mentioned peptides or partial peptides thereof together to give a straight or branched chain product for use in IBP adsorption. In coupling peptides, the coupling may be carried out via a peptide composed of 10 or less residues.

As preferred examples of the coupled peptide, there may be mentioned peptides comprising the amino acid sequence CEQAATSLATLYNLEQYAN (SEQ ID NO:22), CEQAATSLASLFQLDNYAN (SEQ ID NO:23) or CEQMMHNIASLFQLDNYAN (SEQ ID NO:24).

While the above-mentioned peptides as such may be used as adsorbents for IBPs, it is preferred that each adsorbent comprise any of the above-mentioned peptides be immobilized on a water-insoluble carrier. A single species among the above peptides may be immobilized on the carrier. Two or more of the above peptides may be independently selected and immobilized on the carrier.

It is well known to those skilled in the art that conservative substitution is possible at an amino acid position or positions in a peptide or protein without affecting the function thereof. In the case of the present invention, "conservative" substitution means every amino acid replacement within one and the same group consisting of certain specific amino acids. The following may be mentioned as such group of amino acids:
Group I: L, I, V, M, H, W, Y, and F;
Group II: E, Q, D, and N;
Group III: S, T, C, G, A, and P;
Group IV: K, and R.

The above-mentioned peptides can be produced by a method per se known in the art. For example, such as chemical method as the Fmoc or Bmoc method may be used. Alternatively, a biological method may be used; for example, a recombinant organism, preferably a recombinant microorganism, may be used for the expression of a recombinant peptide or protein.

In a preferred mode of embodiment, the peptide capable of binding to IBPs is immobilized in an amount of not smaller than 0.001 nmol but not larger than 100 μmol per milliliter of the water-insoluble carrier.

As the water-insoluble carrier to be used in the practice of the invention, there may be mentioned inorganic carriers such as glass beads and silica gel, organic carriers made of such a synthetic polymer as crosslinked poly(vinyl alcohol), crosslinked polyacrylate, crosslinked polyacrylamide or crosslinked polystyrene or such a polysaccharide as crystalline cellulose, crosslinked cellulose, crosslinked agarose or crosslinked dextran and, further, composite carries such as organic-organic and organic-inorganic composite carries obtained by combining two or more of the carriers mentioned above.

In a further preferred mode of embodiment, the water-insoluble carrier is preferably a hydrophilic one in the adsorption of IBPs. Hydrophilic carriers are preferred since they show relatively low levels of nonspecific binding and good IBP adsorption selectivity. The hydrophilic carrier so referred to herein is a carrier showing an angle of contact with water of not greater than 60 degrees when the carrier-constituting compound is molded into a flat sheet form. As typical examples of such carrier, there may be mentioned carriers made of a polysaccharide such as cellulose, chitosan or dextran, poly(vinyl alcohol), hydrolyzed ethylene-vinyl acetate copolymer, polyacrylamide, poly(acrylic acid), poly(methacrylic acid), poly(methyl methacrylate), poly(acrylic acid)-grafted polyethylene, polyacrylamide-grafted polyethylene, or glass. As commercial products, there may be mentioned, for example, GCL 2000m, which is a porous cellulose gel, and Eupergit C 250L, which is epoxy group-activated polymethacrylamide. The carrier to be used in the practice of the invention is of course not limited to those carried or activated carriers mentioned above. The carriers mentioned above may be used singly or two or more of them as arbitrarily selected may be used in admixture.

The "angle of contact with water" so referred to herein can be determined by preparing a flat film made of the main constituent polymer, forming a liquid drop on that film held in a horizontal state using a microsyringe and measuring the contact angle at room temperature. When the porous material is soluble in an organic solvent, the contact angle can also be measured following dissolution of the porous material and preparation of a cast film on a flat sheet using the resulting solution. For the details of the measurement methods, "Shin Jikken Kagaku Koza (Lectures in Experimental Chemistry, New Series) 18: Kaimen to Koroido (Interface and Colloid)", 1st edition, published Oct. 20, 1977 by Maruzen Co., Ltd., for instance, can be referred to. Thus, a flat sheet/film test specimen having mirror finish smoothness is placed in a horizontal position in an atmosphere filled with a vapor saturated with the liquid to be subjected to measurement, and a liquid drop is formed thereon using a microsyringe. The size of the drop is such that the contact diameter is not larger than about 3 mm (it is also reported that the volume of the drop should be not greater than 0.1 cm$^3$). Generally, the contact angle can be measured using a reading microscope (having a magnification of about 20) equipped with a goniometer. When the lens barrel is inclined downward at an angle of 1 to 2 degrees relative to the horizontal level, the distinctness of the image is markedly improved. The drop is illuminated from ahead with light rays passed through an opal glass sheet or with parallel rays passed through a heat ray-absorbing glass sheet (excerpt from the reference cited above).

In a preferred mode of embodiment, the water-insoluble carrier to be used in the practice of the invention for adsorbing IBPs desirably has a large surface area and preferably has a large number of pores appropriate in size, namely is porous, in view of the intended use and the method of use of the adsorbent according to the invention.

In a preferred mode of embodiment, the water-insoluble porous carrier to be used in adsorbing IBPs shows an exclusion limit molecular weight of not lower than 10,000 but not higher than 10,000,000. Since IBPs are molecules having a molecular weight of not lower than 10,000 but not higher than 1,000,000, it is preferred that the exclusion limit molecular weight be larger than the diameter of each IBP molecule so that antibody molecules may be efficiently adsorbed using the porous carrier. Since, however, when the exclusion limit molecular weight is excessively high, the strength of the carrier decreases and, further, the surface area thereof decreases, a carrier showing an exclusion limit molecular weight of not lower than 100,000 but not higher than 5,000,000 is more preferably used.

With regard to the porous structure of the carrier according to the invention, considering the adsorption capacity per unit volume of the adsorbent, total porosity is preferred to surface porosity, and the carrier having a void volume of not less than 20% and a specific surface area of not less than 3 m$^2$/g is preferred.

Referring to the morphology of the carrier according to the invention, it may assume various forms such as beads, filaments, membranes (inclusive of hollow fiber), and so forth and any of these forms can be liberally chosen. Beads are particularly preferred in view of the circulation of body fluids at the time of extracorporeal circulation. Beads having an average particle diameter of 10 to 2,500 μm are easy to use and those within the size range of 25 μm to 800 μm are preferably used.

Furthermore, the presence of a functional group useful for a ligand coupling reaction on the surface of the carrier according to the invention is advantageous for the purpose of coupling the ligand. Among representative examples of said functional group are hydroxyl, amino, aldehyde, carboxyl, thiol, silanol, amido, epoxy, succinylimido, acid anhydride groups, etc.

The carrier which can be used in the invention may be whichever of a hard carrier and a soft carrier but it is an important factor in its use as an adsorbent for extracorporeal circulation treatment that when it is, for example, packed into a column and a fluid is run thereon, no plugging troubles will take place. For this purpose, a sufficient mechanical strength is required. Therefore, the carrier for use in the invention is more preferably a hard carrier. As used in this specification, the term "hard carrier" means a carrier such that, taking a granular gel as an example, when the gel is evenly packed into a glass cylinder (inside diameter; 9 mm: column length; 150 mm) under the following conditions and a hydrous fluid is passed through the column, the relation between pressure loss ΔP and flow rate is linear up to 0.3 kilogram/cm$^2$. By way of illustration, glass cylindric column (inside diameter; 9 mm: column length; 150 mm) each equipped with a filter having a pore size of 15 μm at either end were uniformly packed with agarose gel (Biogel-A5m, product of Bio-Rad, particle size 50 to 100 mesh), a vinyl polymer gel (TOYOPEARL HW-65, product of TOSOH CORPORATION, particle size 50 to 100 μm), and a cellulose gel (Cellulofine GC-700m, product of Chisso Corporation, particle size 45 to 105 μm), respectively, and using a peristaltic pump, water was passed through each column to determine the relationship of flow rate to pressure loss ΔP (FIG. 1). The flow rate (cm/min.) was plotted on the ordinate and the pressure loss (kg/cm$^2$) was plotted on the abscissa. In the figure, ○ represents TOYOPEARL HW-65, Δ Cellulofine GC-700m, and ● Biogel-A5m. It was found that whereas the flow rate was increased in approximate proportion to the pressure gain in the cases of TOYOPEARL HW-65 and Cellulofine GC-700m, compaction occurred in the case of Biogel-A5m so that increasing the pressure did not increase the flow rate.

In immobilizing an insulin-binding protein or peptide to the carrier according to the invention, it is more preferable to improve the adsorption efficiency through reducing the steric hindrance of the protein or peptide and, for suppression of non-specific adsorption, immobilize the protein or peptide through a hydrophilic spacer.

The spacer so referred to herein is a compound for intentionally separating the carrier from the ligand. The linker so referred to herein is a compound binding the carrier to the ligand. As the hydrophilic spacer, a poly(alkylene oxide) derivative as substituted with a carboxyl, amino, aldehyde, epoxy or the like group at either terminus, etc. is preferably used. A peptide or amino acid is also used as the linker or spacer in some instances. The spacer or linker or a fluorescent label can be bound to the amino terminus and/or carboxyl terminus of the peptide of the invention.

In the present invention, the methods of immobilizing the peptide capable of binding to IBPs, which is to be introduced into the carrier, and the organic compound spacer are not particularly restricted but include those immobilization methods which are generally employed in immobilizing proteins or peptides on carriers and based, for example, on the epoxy reaction, the nick base reaction, the condensation reaction using a carbodiimide reagent or the like, the active ester reaction, or the carrier crosslinking reaction using a glutaraldehyde reagent or the like. Further, considering that the adsorbent is one capable of being used in extracorporeal circulation treatment and hemopurification, those immobilization methods that hardly allows the protein to be released from the carrier on the occasion of sterilization of the adsorbent and/or treatment are more preferably applied.

Thus, for example, mention may be made of (1) the method comprising reacting the carboxyl group of the carrier with N-hydroxysuccinimide and then reacting the resulting substituent succinimidoxycarbonyl group with the amino group of the protein or peptide (active ester method), (2) the method comprising subjecting the amino or carboxyl group of the carrier and the carboxyl or amino group of the protein or peptide to condensation reaction in the presence of a condensation reagent such as dicyclohexylcarbodiimide (condensation method) and (3) the method comprising crosslinking the protein or peptide using a compound having two or more functional groups, for example glutaraldehyde (single substance crosslinking method), among others. For preventing protein release and elution as far as possible, binding via covalent bonding is preferred.

In a preferred mode of embodiment, the adsorbent of the invention is used for adsorbing IBPs occurring in blood, plasma or some other body fluid. More particularly, a variety of methods are available for bringing the carrier with a peptide capable of binding to IBPs as immobilized thereon into contact with body fluids such as blood, plasma or serum to adsorb IBPs in body fluids. Among representative methods are (1) the method which comprises withdrawing body fluids and pooling it in a bag or the like, mixing it with the adsorbent to adsorb IBPs thereon, and filtering off the adsorbent to recover the body fluids deprived of IBPs and (2) the method which comprises filling the adsorbent into a container having a body fluid inlet and a body fluid outlet and equipped with a filter which is permeable to the body fluids but impermeable to the adsorbent at said outlet and passing the body fluids through the container. Although whichever of the methods can be used, the adsorbent of the invention is suited to the latter method which is simple procedure-wise, and by applying it to an extracorporeal circuit, IBPs can be removed from the patient's body fluid efficiently on line.

The IBP adsorber of the invention comprises any of the adsorbents described hereinabove as contained in a container having a liquid inlet and a liquid outlet and is provided with means for preventing the adsorbent from flowing out of the container. As an example, the adsorber for IBPs of the present invention using the adsorbent adsorbing IBPs is explained on the basis of its schematic sectional view. Adsorber 7 shown in FIG. 2 comprises a liquid inlet or outlet 1, a liquid inlet or outlet 2, an IBP adsorbent 3 of the present invention, means for preventing the adsorbent from flowing out 4 and 5 through which liquid and components contained in the liquid can pass but the adsorbent for IBPs cannot pass, and a column 6. The shape and material of this container are not particularly restricted, but preferably, for example, a tube container having a content of about 20 to 400 mL and a diameter of about 2 to 10 cm may be used.

The method of adsorbing IBPs according to the invention comprises the step of contacting any of the adsorbents described hereinabove with an IBP-containing liquid.

In a preferred mode of embodiment, the IBP-containing liquid is blood, plasma or some other body fluid.

The ability of the peptide or adsorbent to adsorb IBPs is evaluated, for example, in the following manner.

Peptide Evaluation

The affinity for the soluble insulin receptor identified by SEQ ID NO:1 is compared by the method using BIAcore (BIAcore AB) (as described in Am. J. Physiol. 272 (1997) E1089-1098). Briefly, a solution of the soluble insulin receptor is brought into contact with the surface of the ready-made sensor chip with the peptide defined by SEQ ID NO:1 as immobilized thereon, and the interaction is measured.

Adsorbent Evaluation

Healthy human serum (300 μl) supplemented with the soluble insulin receptor is added to the peptide synthesized, the mixture is shaken at 37 degrees for 2 hours, the insulin receptor in the supernatant is assayed by the RIA method (described in Am. J. Physiol. 257 (1989) E451-457), and the adsorption percentage is calculated as follows:

$$\text{Adsorption percentage (\%)} = (1 - \text{postreaction } A \text{ concentration/prereaction } A \text{ concentration}) \times 100$$

Here, A stands for the soluble insulin receptor.

EXPLANATION OF SYMBOLS

Figure 1:
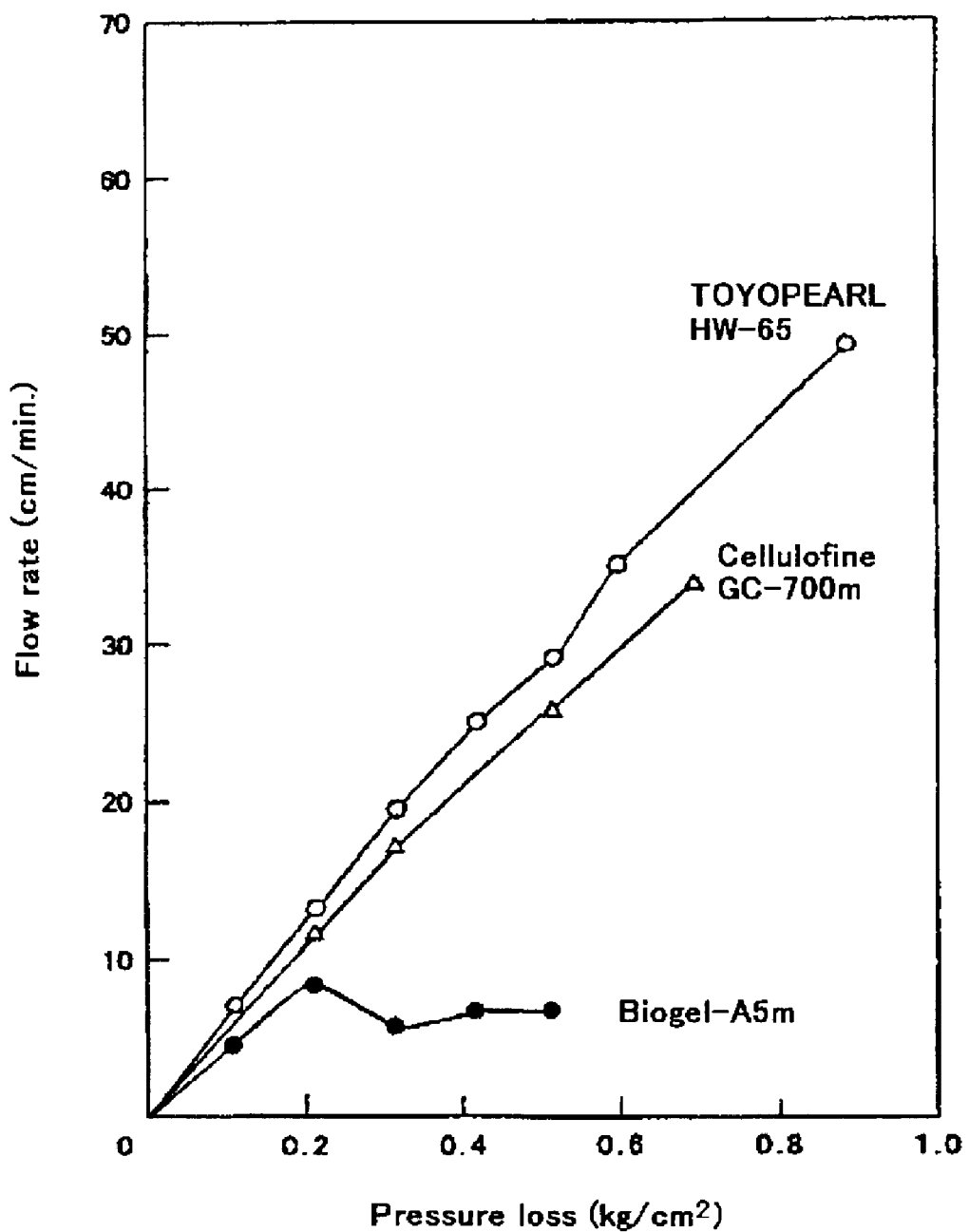
FIG. 1 is a graphic representation of the results of an investigation as to the relation between flow rate and pressure loss using three gel species.
Figure 2:
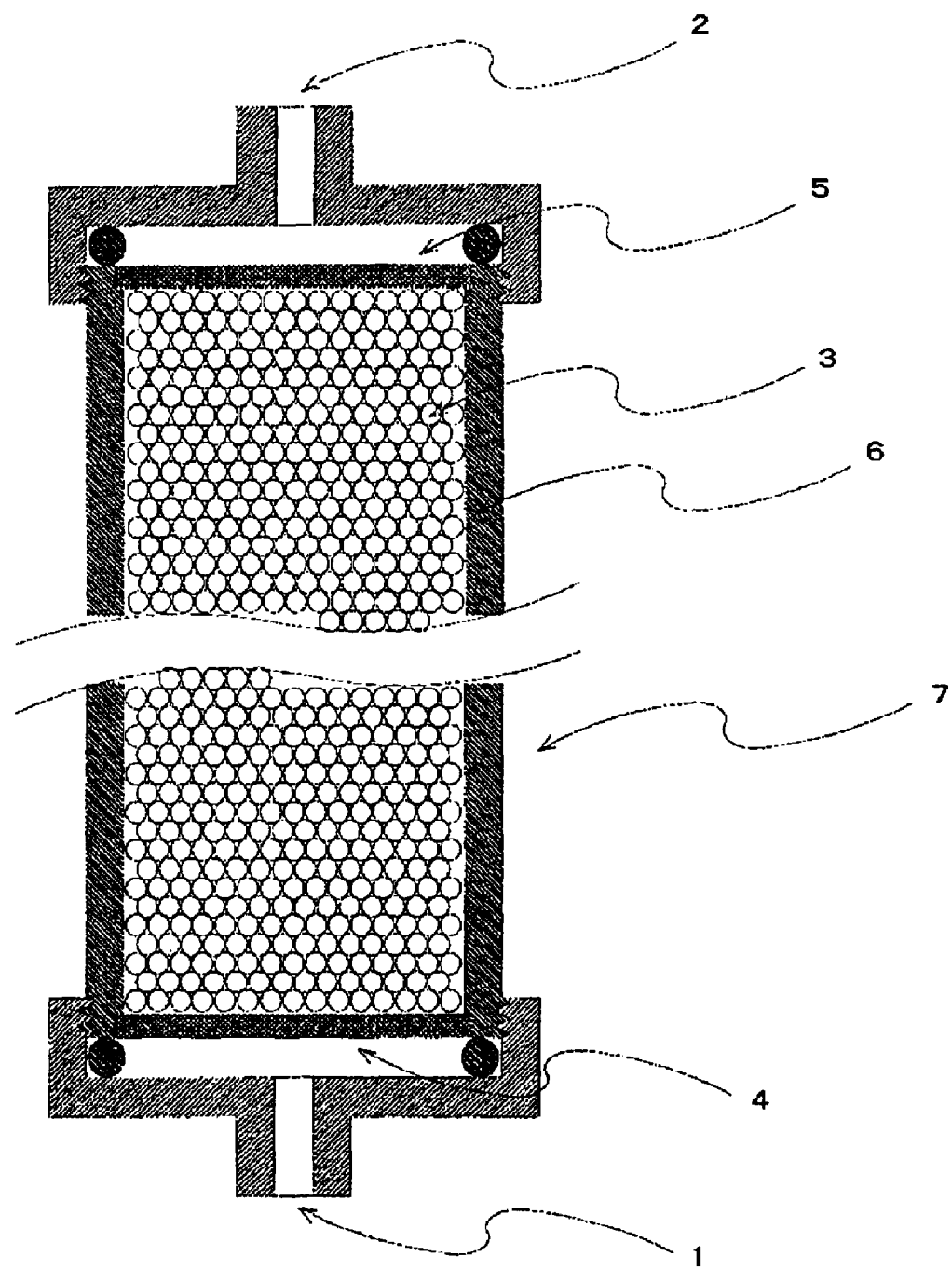
FIG. 2 is a schematic sectional view of an example of the IBP adsorber according to the invention.

1—Body fluid inlet
2—Body fluid outlet
3—IBP adsorbent
4, 5—Filters allowing the passage of body fluids and the components contained in body fluids but not allowing the passage of the IBP adsorbent.
6—Column
7—Adsorber

BEST MODE FOR CARRYING OUT THE INVENTION

The following examples illustrate the present invention in further detail. These examples are, however, by no means limitative of the scope of the invention.

EXAMPLE 1

Preparation of Peptide P2 and Adsorbent 1 (GCL 2000m-P2)

A peptide having the amino acid sequence CQLDNYAN (SEQ ID NO:2) was chemically synthesized by the Fmoc method. The crude peptide obtained was dissolved in 0.1% trifluoroacetic acid and then purified by high-performance liquid chromatography using a reversed phase column (μBondasphere C18, Nihon Millipore Waters K.K.) (peptide P2).

Water was added to 90 ml of GCL-2000m (exclusion limit molecular weight for spherical proteins: 3,000,000, Chisso Corporation), a cellulosic porous hard gel, to make the whole amount 180 ml, 60 ml of 2 M sodium hydroxide was then added, and the mixture was warmed to 40 degrees. Thereto was added 21 ml of epichlorohydrin, and the reaction was allowed to proceed under stirring at 40 degrees for 1 hour. After completion of the reaction, the gel was thoroughly washed with water, whereby an epoxy-activated cellulose gel was obtained. The above-mentioned peptide P2 (0.5 mg) was dissolved in 0.5 ml of 0.05 M borate buffer (pH 10.0), the solution was readjusted to pH 10 by adding a 0.01 N aqueous solution of sodium hydroxide and the total amount was made 1.0 ml (peptide solution). The peptide solution was added to 0.4 ml of the above-mentioned epoxy-activated GCL 2000m, the mixture was shaken at 37 degrees for 5 hours, and the solid was washed with a sufficient amount of PBS (10 mM phosphate buffer containing 150 mM sodium chloride) to give the adsorbent 1 (GCL 2000m-P2).

EXAMPLE 2

Preparation of Peptide P8 and Adsorbent 2 (Sepharose 4B-P8)

A peptide having the amino acid sequence CEQAATS (SEQ ID NO:8) was synthesized and purified in the same manner as in Example 1 (Peptide 8).

To pretreated CNBr-activated Sepharose 4B (exclusion limit molecular weight for spherical proteins: >20,000,000, Amersham Biosciences K.K.) (2.0 ml) was added a solution of 20 mg of the above-mentioned peptide P8 in 5.0 ml of Coupling Buffer (peptide solution), and the coupling reaction was allowed to proceed according to the manual attached to the product to give the adsorbent 2 (Sepharose 4B-P8).

EXAMPLE 3

Preparation of Peptide P14 and Adsorbent 3 (Kac-P14)

A peptide having the amino acid sequence CASDIVEGLYIVLAER (SEQ ID NO:14) was synthesized and purified in the same manner as in Example 1 (Peptide 14).

Water was added to 90 ml of Kac (exclusion limit molecular weight for spherical proteins: 5,000,000, a prototype of KANEKA CORPORATION), a cellulosic porous hard gel, to make the whole amount 180 ml, 60 ml of 2 M sodium hydroxide was then added, and the mixture was warmed to 40 degrees. Thereto was added 21 ml of epichlorohydrin, and the reaction was allowed to proceed under stirring at 40 degrees for 1 hour. After completion of the reaction, the gel was thoroughly washed with water, whereby an epoxy-activated cellulose gel was obtained. The above-mentioned peptide P14 (50 mg) was dissolved in 2.0 ml of 0.05 M borate buffer (pH 10.0), the solution was readjusted to pH 10 by adding a 0.01 N aqueous solution of sodium hydroxide and the total amount was made 4.0 ml (peptide solution). The peptide solution was added to 0.5 ml of the above-mentioned epoxy-activated Kac, the mixture was shaken at 37 degrees for 2 hours, and the solid was washed with a sufficient amount of PBS (10 mM phosphate buffer containing 150 mM sodium chloride) to give the adsorbent 3 (Kac-P14).

EXAMPLE 4

Preparation of Adsorbent 4 (Sepharose 4B-P5)

A peptide having the amino acid sequence CGLDNGLDN (SEQ ID NO:5) was synthesized and purified in the same manner as in Example 1 (Peptide 5).

To pretreated EAH Sepharose 4B (exclusion limit molecular weight for spherical proteins: >20,000,000, Amersham Biosciences K.K.) (0.4 ml) was added a solution of 8.0 mg of the above-mentioned peptide P5 in 3.0 ml of Coupling Buffer (peptide solution), and the coupling reaction was allowed to proceed according to the manual attached to the product to give the adsorbent 4 (Sepharose 4B-P5).

EXAMPLE 5

Preparation of Peptide P22 and Adsorbent 5 (Kac-P22)

A peptide having the amino acid sequence CEQAATSLATLYNLEQYAN (SEQ ID NO:22) was synthesized and purified in the same manner as in Example 1 (Peptide 22).

90 ml of an epoxy-activated cellulose gel of Kac (a prototype of KANEKA CORPORATION) was obtained in the same manner as in Example 3. The above-mentioned peptide P22 (50 mg) was dissolved in 2.0 ml of 0.05 M borate buffer (pH 10.0), the solution was readjusted to pH 10 by adding a 0.01 N aqueous solution of sodium hydroxide and the total amount was made 5.0 ml (peptide solution). The peptide solution was added to 1.0 ml of the above-mentioned epoxy-activated Kac, the mixture was shaken at 37 degrees for 3 hours, and the solid was washed with a sufficient amount of PBS (10 mM phosphate buffer containing 150 mM sodium chloride) to give the adsorbent 5 (Kac-P22).

EXAMPLE 6

Synthesis of Peptide P15

A peptide having the amino acid sequence CASDIVEG-IYL (SEQ ID NO:15) was synthesized and purified in the same manner as in Example 1 (Peptide 15).

EXAMPLE 7

Synthesis of Peptide P21

A peptide having the amino acid sequence CQHILGSDI-VEGIYL (SEQ ID NO:21) was synthesized and purified in the same manner as in Example 1 (Peptide 21).

EXAMPLE 8

IBP-Binding Ability of Peptide P14

The dissociation constant (KD) of the peptide P14 obtained in Example 3 was determined using BIAcore upgrade (Biacore AB) and the analysis software BIA evaluation version 3.0 (Biacore AB).

The ligand was immobilized on the sensor chip CM5 research grade (Biacore AB) by the amine coupling method. Thus, the peptide mentioned above was dissolved in 20 mM carbonate buffer (pH 8.5) (500 µg/ml), and 100 µl of the solution was passed through the flow cell at a flow rate of 5 µl/min. The amount of the peptide immobilized was 200 RU (resonance units).

Recombinant Human Insulin Receptor (28-956) (GT/TECHNE Corp.) was used as the analyte soluble insulin receptor (SIR). To 50 mg in a vial was added HBS-EP buffer (250 ml) for thorough dissolution (1,000 mM solution), and the solution was 10-fold diluted to give a 100 nM solution. Eight concentration levels from 100 nM to 0.781 nM were prepared by subsequent repetitions of doubling dilution, and measurements were carried out using HBS-EP buffer (10 mM HEPES pH 7.4, 0.15M NaCl, 3 mM EDTA, 0.005% Surfactant P20) (Biacore AB) as a running solution; the rate of flow was 10 µl/min. A sensorgram was thus obtained.

Fitting was carried out for the sensorgram obtained, and the dissociation constant KD=1.6E–06 was obtained from the peptide-SIR binding rate constant (9.7E+03) and dissociation rate constant (1.5E02).

EXAMPLE 9

IBP-Binding Ability of Peptide P15

The dissociation constant (KD) of the peptide P15 obtained in Example 6 was determined using BIAcore upgrade (Biacore AB) and the analysis software BIA evaluation version 3.0 (Biacore AB).

The ligand was immobilized on the sensor chip CM5 research grade (Biacore AB) by the amine coupling method. Thus, the peptide mentioned above was dissolved in 20 mM carbonate buffer (pH 8.5) (500 µg/ml), and 100 µl of the solution was passed through the flow cell at a flow rate of 5 µl/min. The amount of the peptide immobilized was 130 RU.

Recombinant Human Insulin Receptor (28-956) (GT/TECHNE Corp.) was used as the analyte SIR. Eight concentration levels from 100 nM to 0.781 nM were prepared by subsequent repetitions of doubling dilution, which was started from diluting 100 nM solution, and measurements were carried out using HBS-EP buffer as a running solution; the rate of flow was 10 µl/min. A sensorgram was thus obtained.

Fitting was carried out for the sensorgram obtained, and the dissociation constant KD=2.4E–05 was obtained from the peptide-SIR binding rate constant (8.6E+02) and dissociation rate constant (2.0E–02).

EXAMPLE 10

IBP-Binding Ability of Peptide P21

The dissociation constant (KD) of the peptide P21 obtained in Example 7 was determined using BIAcore upgrade (Biacore AB) and the analysis software BIA evaluation version 3.0 (Biacore AB).

The ligand was immobilized on the sensor chip CM5 research grade (Biacore AB) by the amine coupling method. Thus, the peptide mentioned above was dissolved in 20 mM carbonate buffer (pH 8.5) (500 µg/ml), and 100 µl of the solution was passed through the flow cell at a flow rate of 5 µl/min. The amount of the peptide immobilized was 270 RU.

Recombinant Human Insulin Receptor (28-956) (GT/TECHNE Corp.) was used as the analyte SIR. Eight concentration levels from 100 nM to 0.781 nM were prepared by subsequent repetitions of doubling dilution, which was started from diluting 100 nM solution, and measurements were carried out using HBS-EP buffer as a running solution; the rate of flow was 10 µl/min. A sensorgram was thus obtained.

Fitting was carried out for the sensorgram obtained, and the dissociation constant KD=1.2E–05 was obtained from the peptide-SIR binding rate constant (5.1E+04) and dissociation rate constant (6.0E–01).

The results obtained in Examples 8 to 10 are summarized in Table 1 below. The dissociation constant (KD) values for the SIR as obtained in Examples 8 to 10 are not higher than 1.0E–04 and, therefore, the peptides have sufficient levels of binding ability for their use as ligands for IBP adsorption.

TABLE 1

| | Peptide | Binding rate constant | Dissociation rate constant | Dissociation constant (KD) |
|---|---|---|---|---|
| Example 8 | P14 (SEQ ID NO: 14) | 9.7E+03 | 1.5E–02 | 1.6E–06 |
| Example 9 | P15 (SEQ ID NO: 15) | 8.6E+02 | 2.0E–02 | 2.4E–05 |
| Example 10 | P21 (SEQ ID NO: 21) | 5.1E+04 | 6.0E–01 | 1.2E–05 |

INDUSTRIAL APPLICABILITY

The present invention can be utilized in improving the condition of insulin resistance, which is causative mainly of diabetes and other diseases, by utilizing various peptides having IBP-binding ability, and drugs, adsorbents and the like prepared by using those peptides, as disclosed herein.

The invention claimed is:

1. A peptide which comprises the amino acid sequence of SEQ ID NO: 14.

2. An adsorbent for insulin-binding proteins which comprises the peptide according to claim 1 immobilized on a water-insoluble carrier.

3. The adsorbent for insulin-binding proteins according to claim 2, wherein the water-insoluble carrier is porous.

4. The adsorbent for insulin-binding proteins according to claim 2, wherein the water-insoluble carrier is hydrophilic.

* * * * *

SEQUENCE LISTING

```
<160> NUMBER OF SEQ ID NOS: 24

<210> SEQ ID NO 1
<211> LENGTH: 7
<212> TYPE: PRT
<213> ORGANISM: Homo sapiens

<400> SEQUENCE: 1

Gln Leu Glu Asn Tyr Cys Asn
1               5

<210> SEQ ID NO 2
<211> LENGTH: 8
<212> TYPE: PRT
<213> ORGANISM: Artificial
<220> FEATURE:
<223> OTHER INFORMATION: chemically synthesized

<400> SEQUENCE: 2

Cys Gln Leu Asp Asn Tyr Ala Asn
1               5

<210> SEQ ID NO 3
<211> LENGTH: 8
<212> TYPE: PRT
<213> ORGANISM: Artificial
<220> FEATURE:
<223> OTHER INFORMATION: chemically synthesized

<400> SEQUENCE: 3

Cys Asn Leu Glu Gln Tyr Ala Asn
1               5

<210> SEQ ID NO 4
<211> LENGTH: 8
<212> TYPE: PRT
<213> ORGANISM: Artificial
<220> FEATURE:
<223> OTHER INFORMATION: chemically synthesized

<400> SEQUENCE: 4

Cys Gly Leu Glu Gly Thr Met Asn
1               5

<210> SEQ ID NO 5
<211> LENGTH: 9
<212> TYPE: PRT
<213> ORGANISM: Artificial
<220> FEATURE:
<223> OTHER INFORMATION: chemically synthesized

<400> SEQUENCE: 5

Cys Gly Leu Asp Asn Gly Leu Asp Asn
1               5

<210> SEQ ID NO 6
<211> LENGTH: 7
<212> TYPE: PRT
<213> ORGANISM: Artificial
<220> FEATURE:
<223> OTHER INFORMATION: chemically synthesized

<400> SEQUENCE: 6

Leu Glu Asn Ala Leu Glu Asn
1               5
```

```
<210> SEQ ID NO 7
<211> LENGTH: 8
<212> TYPE: PRT
<213> ORGANISM: Homo sapiens

<400> SEQUENCE: 7

Glu Gln Cys Cys Thr Ser Ile Cys
1               5

<210> SEQ ID NO 8
<211> LENGTH: 7
<212> TYPE: PRT
<213> ORGANISM: Artificial
<220> FEATURE:
<223> OTHER INFORMATION: chemically synthesized

<400> SEQUENCE: 8

Cys Glu Gln Ala Ala Thr Ser
1               5

<210> SEQ ID NO 9
<211> LENGTH: 7
<212> TYPE: PRT
<213> ORGANISM: Artificial
<220> FEATURE:
<223> OTHER INFORMATION: chemically synthesized

<400> SEQUENCE: 9

Cys Glu Gln Ala Gly Thr Ser
1               5

<210> SEQ ID NO 10
<211> LENGTH: 7
<212> TYPE: PRT
<213> ORGANISM: Artificial
<220> FEATURE:
<223> OTHER INFORMATION: chemically synthesized

<400> SEQUENCE: 10

Cys Glu Gln Met Met His Asn
1               5

<210> SEQ ID NO 11
<211> LENGTH: 6
<212> TYPE: PRT
<213> ORGANISM: Artificial
<220> FEATURE:
<223> OTHER INFORMATION: chemically synthesized

<400> SEQUENCE: 11

Glu Gln Cys Cys His Asn
1               5

<210> SEQ ID NO 12
<211> LENGTH: 16
<212> TYPE: PRT
<213> ORGANISM: Homo sapiens

<400> SEQUENCE: 12

Cys Gly Ser His Leu Val Glu Ala Leu Tyr Leu Val Cys Gly Glu Arg
1               5                   10                  15

<210> SEQ ID NO 13
<211> LENGTH: 16
<212> TYPE: PRT
<213> ORGANISM: Artificial
<220> FEATURE:
```

-continued

<223> OTHER INFORMATION: chemically synthesized

<400> SEQUENCE: 13

Cys Gly Ser Asp Leu Val Glu Val Ala Tyr Leu Gly Gly Glu Arg
1               5                   10                  15

<210> SEQ ID NO 14
<211> LENGTH: 16
<212> TYPE: PRT
<213> ORGANISM: Artificial
<220> FEATURE:
<223> OTHER INFORMATION: chemically synthesized

<400> SEQUENCE: 14

Cys Ala Ser Asp Ile Val Glu Gly Leu Tyr Ile Val Leu Ala Glu Arg
1               5                   10                  15

<210> SEQ ID NO 15
<211> LENGTH: 11
<212> TYPE: PRT
<213> ORGANISM: Artificial
<220> FEATURE:
<223> OTHER INFORMATION: chemically synthesized

<400> SEQUENCE: 15

Cys Ala Ser Asp Ile Val Glu Gly Ile Tyr Leu
1               5                   10

<210> SEQ ID NO 16
<211> LENGTH: 16
<212> TYPE: PRT
<213> ORGANISM: Artificial
<220> FEATURE:
<223> OTHER INFORMATION: chemically synthesized

<400> SEQUENCE: 16

Cys Ala Ser His Ile Val Glu Gly Ile Tyr Leu Ile Leu Ala Glu Arg
1               5                   10                  15

<210> SEQ ID NO 17
<211> LENGTH: 16
<212> TYPE: PRT
<213> ORGANISM: Artificial
<220> FEATURE:
<223> OTHER INFORMATION: chemically synthesized

<400> SEQUENCE: 17

Cys Ala Ser His Ile Val Glu Gly Leu Tyr Ile Val Cys Ala Glu Arg
1               5                   10                  15

<210> SEQ ID NO 18
<211> LENGTH: 16
<212> TYPE: PRT
<213> ORGANISM: Artificial
<220> FEATURE:
<223> OTHER INFORMATION: chemically synthesized

<400> SEQUENCE: 18

Cys Ala Ser His Ile Val Glu Gly Ile Tyr Leu Ala Cys Gly Asp Arg
1               5                   10                  15

<210> SEQ ID NO 19
<211> LENGTH: 15
<212> TYPE: PRT
<213> ORGANISM: Artificial
<220> FEATURE:
<223> OTHER INFORMATION: chemically synthesized -continued

```
<400> SEQUENCE: 19

Gly Ser Asp Ile Val Glu Gly Leu Tyr Ile Val Cys Ala Glu Arg
1               5                   10                  15

<210> SEQ ID NO 20
<211> LENGTH: 15
<212> TYPE: PRT
<213> ORGANISM: Artificial
<220> FEATURE:
<223> OTHER INFORMATION: chemically synthesized

<400> SEQUENCE: 20

Gly Ser Asp Ile Val Glu Gly Ile Tyr Leu Ala Leu Gly Glu Lys
1               5                   10                  15

<210> SEQ ID NO 21
<211> LENGTH: 15
<212> TYPE: PRT
<213> ORGANISM: Artificial
<220> FEATURE:
<223> OTHER INFORMATION: chemically synthesized

<400> SEQUENCE: 21

Cys Gln His Ile Leu Gly Ser Asp Ile Val Glu Gly Ile Tyr Leu
1               5                   10                  15

<210> SEQ ID NO 22
<211> LENGTH: 19
<212> TYPE: PRT
<213> ORGANISM: Artificial
<220> FEATURE:
<223> OTHER INFORMATION: chemically synthesized

<400> SEQUENCE: 22

Cys Glu Gln Ala Ala Thr Ser Leu Ala Thr Leu Tyr Asn Leu Glu Gln
1               5                   10                  15

Tyr Ala Asn

<210> SEQ ID NO 23
<211> LENGTH: 19
<212> TYPE: PRT
<213> ORGANISM: Artificial
<220> FEATURE:
<223> OTHER INFORMATION: chemically synthesized

<400> SEQUENCE: 23

Cys Glu Gln Ala Ala Thr Ser Leu Ala Ser Leu Phe Gln Leu Asp Asn
1               5                   10                  15

Tyr Ala Asn

<210> SEQ ID NO 24
<211> LENGTH: 19
<212> TYPE: PRT
<213> ORGANISM: Artificial
<220> FEATURE:
<223> OTHER INFORMATION: chemically synthesized

<400> SEQUENCE: 24

Cys Glu Gln Met Met His Asn Ile Ala Ser Leu Phe Gln Leu Asp Asn
1               5                   10                  15

Tyr Ala Asn
```